United States Patent
Moore et al.

(10) Patent No.: US 9,912,113 B2
(45) Date of Patent: Mar. 6, 2018

(54) SYSTEMS AND METHODS FOR IMPLEMENTING AN ELECTRICAL ROTARY JOINT IN A LARGE-DIAMETER SYSTEM USING SMALL-DIAMETER CAPSULE SLIP RINGS

(71) Applicant: Morpho Detection, LLC, Newark, CA (US)

(72) Inventors: Jared William Moore, Oakland, CA (US); Steven Leslie Hills, San Jose, CA (US)

(73) Assignee: Morpho Detection, LLC, Newark, CA (US)

( * ) Notice: Subject to any disclaimer, the term of this patent is extended or adjusted under 35 U.S.C. 154(b) by 0 days.

(21) Appl. No.: 15/046,151

(22) Filed: Feb. 17, 2016

(65) Prior Publication Data
US 2017/0237217 A1   Aug. 17, 2017

(51) Int. Cl.
| H01R 39/28 | (2006.01) |
| A61B 6/03 | (2006.01) |
| A61B 6/00 | (2006.01) |
| F16H 13/02 | (2006.01) |

(52) U.S. Cl.
CPC ............. *H01R 39/28* (2013.01); *A61B 6/032* (2013.01); *A61B 6/56* (2013.01); *F16H 13/02* (2013.01)

(58) Field of Classification Search
CPC ........ H01R 39/00; H01R 39/02; H01R 39/08; H01R 39/085; H01R 39/12; H01R 39/14; H01R 39/18; H01R 39/28; H01R 39/32; H01R 39/34; H01R 39/56; H01R 35/00; A61B 6/56

USPC .......................................................... 439/13
See application file for complete search history.

(56) References Cited

U.S. PATENT DOCUMENTS

| 1,243,286 A | 10/1917 | Gscheidlen |
| 1,845,115 A | 2/1932 | Apple |
| 2,473,526 A * | 6/1949 | Hood ............... H01R 39/00 191/1 R |

(Continued)

FOREIGN PATENT DOCUMENTS

| JP | S59207133 A | 11/1984 |
| WO | 2012041554 A1 | 4/2012 |
| WO | 2014073828 A1 | 5/2014 |

OTHER PUBLICATIONS

European Search Report, Application No. 17000241.4, dated Aug. 4, 2017, 7 pps.

Primary Examiner — Harshad C Patel
(74) Attorney, Agent, or Firm — Armstrong Teasdale LLP (57) ABSTRACT

A system for implementing an electrical rotary joint in a large-diameter system using relatively small-diameter capsule slip rings is described herein. The system includes a system rotor that rotates about a system axis of rotation, and a system stator that is stationary with respect to the system rotor. The system also includes at least one conductive contact channel disposed on one of the system rotor and the system stator. The system further includes at least one capsule slip ring (CSR) coupled to the other of the system rotor and the system stator. The at least one CSR has a conductive annular element coupled thereto, the conductive annular element in mechanical contact with the at least one conductive contact channel such that the at least one CSR forms an electrical rotary joint between the system rotor and the system stator.

7 Claims, 7 Drawing Sheets

(56) References Cited

U.S. PATENT DOCUMENTS

| | | | | |
|---|---|---|---|---|
| 3,398,387 | A | * | 8/1968 | Wendell .................. G01C 19/10 29/597 |
| 3,652,971 | A | * | 3/1972 | Bugg ..................... H01R 39/00 439/10 |
| 4,447,752 | A | * | 5/1984 | Boyce .................... H01R 39/24 310/232 |
| 4,856,323 | A | * | 8/1989 | Morishita ................ B62D 6/10 73/117.02 |
| 6,012,935 | A | * | 1/2000 | Bolen .................. B60R 16/027 439/15 |
| 9,093,808 | B2 | * | 7/2015 | Holzapfel .............. H01R 39/08 |
| 9,291,417 | B2 | * | 3/2016 | James ..................... F41A 21/30 |
| 9,304,015 | B2 | * | 4/2016 | Angerpointner ....... H01R 39/08 |
| 9,391,417 | B2 | * | 7/2016 | Zacharko .............. H01R 39/46 |
| 2005/0135551 | A1 | * | 6/2005 | Katcha ................... A61B 6/032 378/15 |
| 2009/0046913 | A1 | * | 2/2009 | Chandra ................ A61B 6/035 382/131 |
| 2011/0081789 | A1 | * | 4/2011 | Schlichtherle ......... H01R 39/64 439/28 |
| 2012/0043850 | A1 | | 2/2012 | Zhang et al. |

\* cited by examiner

SYSTEMS AND METHODS FOR IMPLEMENTING AN ELECTRICAL ROTARY JOINT IN A LARGE-DIAMETER SYSTEM USING SMALL-DIAMETER CAPSULE SLIP RINGS

BACKGROUND

The embodiments described herein relate generally to rotary joints, and more particularly, to electrical connections across rotatory joints formed by small-diameter capsule slip rings (CSR) as implemented in computed tomography (CT) gantry systems.

Slip rings are used to transmit electrical signals—either data or power—across a rotatory joint to/from a stationary platform from/to a rotating one. Slip rings that require a large thru-bore, like those used on computed tomography (CT) scanners, may be one of the more expensive components in a CT system. At least some known slip rings wear and fail due to the effects of kinetic friction at the contact point of the rotary joint (which is substantially an entire inner surface of the large thru-bore slip ring in these systems). Failure of a slip ring in the field can trigger an expensive process that requires shipment and installation of rigging to remove and/or support parts of the CT rotating gantry so that the slip ring may be removed and repaired or replaced. Accordingly, it would be beneficial to have a CT system in which large thru-bore slip rings are replaced with an alternative component that is more easily replaced and/or repaired.

BRIEF SUMMARY

In one aspect, a system is provided, the system including a system rotor that rotates about a system axis of rotation and a system stator that is stationary with respect to the system rotor. The system also includes at least one conductive contact channel disposed on one of the system rotor and the system stator. The system further includes at least one capsule slip ring (CSR) coupled to the other of the system rotor and the system stator. The at least one CSR has a conductive annular element coupled thereto, the conductive annular element in mechanical contact with the at least one conductive contact channel such that the at least one CSR forms an electrical rotary joint between the system rotor and the system stator.

In another aspect, a gantry system is provided, the gantry system including a gantry that rotates about a system axis of rotation and a frame that is stationary with respect to the gantry. The gantry system also includes at least one conductive contact channel disposed on one of the gantry and the frame. The gantry system further includes at least one capsule slip ring (CSR) coupled to the other of the gantry and the frame. The at least one CSR has a contact roller wheel (CRW) coupled thereto, the CRW in mechanical contact with the at least one conductive contact channel such that the at least one CSR forms an electrical rotary joint between the gantry and the frame.

In yet another aspect, a method of implementing an electrical rotary joint between a system rotor and a system stator is provided. The method includes coupling the system rotor to the system stator. The system rotor is configured to rotate about a system axis of rotation. The method also includes coupling at least one conductive contact channel to one of the system rotor and the system stator, and coupling at least one capsule slip ring (CSR) to the other of the system rotor and the system stator. The method further includes coupling a conductive annular element to the at least one CSR, and biasing the conductive annular element against the at least one conductive contact channel, such that the at least one CSR forms the electrical rotary joint between the system rotor and the system stator.

DETAILED DESCRIPTION

The gantry system described herein includes a large-diameter gantry having a plurality of small-diameter capsule slips rings (CSRs) positioned therearound. More specifically, the CSRs contact a contact channel disposed about a circumference of the gantry. The CSRs permit communication (e.g., data transfer or power transfer) across the contact channel between a stationary component and a rotating component of the gantry system. In some embodiments, the CSRs are coupled to a stationary gantry and contact a stationary contact channel disposed about the circumference of the gantry and spaced a distance therefrom. In other embodiments, the CSRs are coupled to a stationary component spaced from a rotating gantry and contact a contact channel disposed directly about the circumference of the gantry. The small-diameter CSRs replace large thru-bore slip rings of other gantry systems, and are more easily accessed and removed for replacement or repair. Moreover, the small-diameter CSRs function to eliminate the effects of kinetic friction at the contact point of the rotary joint by providing a rolling contact, which produces only static friction, thereby reducing wear on the CSRs compared to large thru-bore slip ring systems. Accordingly, the CSRs provide an alternative rotary joint without the above-described problems with large thru-bore slip rings.

As used herein, the terms "large diameter" and "small diameter" are relative terms in that "small diameter" refers to diameters smaller than any "large diameter." In one example embodiment, although not meant to limit the scope of the present disclosure, a "large-diameter system rotor" or "large-diameter gantry" may refer to a system rotor or gantry having a diameter from about 0.25 m to 50 m, or, more particularly, from about 0.5 m to about 1.5 m. Moreover, in another example embodiment, although not meant to limit the scope of the present disclosure, a "small-diameter CSR" may refer to a CSR having a diameter between about 1 cm to about 25 cm, or, more particularly, from about 1 cm to about 10 cm.

As used herein, "CSR stator" refers generally to component(s) of a CSR intended to be stationary. However, the CSR stator may be in motion relative to the system stator. "CSR rotor" refers generally to component(s) of a CSR intended to rotate relative to the CRS stator. "CSR" or "CSR system" refers generally to the high-level electrical rotary joint being implemented between the stationary and rotating components of the gantry system. A CSR system may be composed of a plurality of CSRs and/or "lesser" rotary joints (e.g., those implemented within an individual CSR). "System stator" refers generally to the gantry system's overall stationary component(s). "System rotor" refers generally to the gantry system's rotating component(s).

Figure 1:
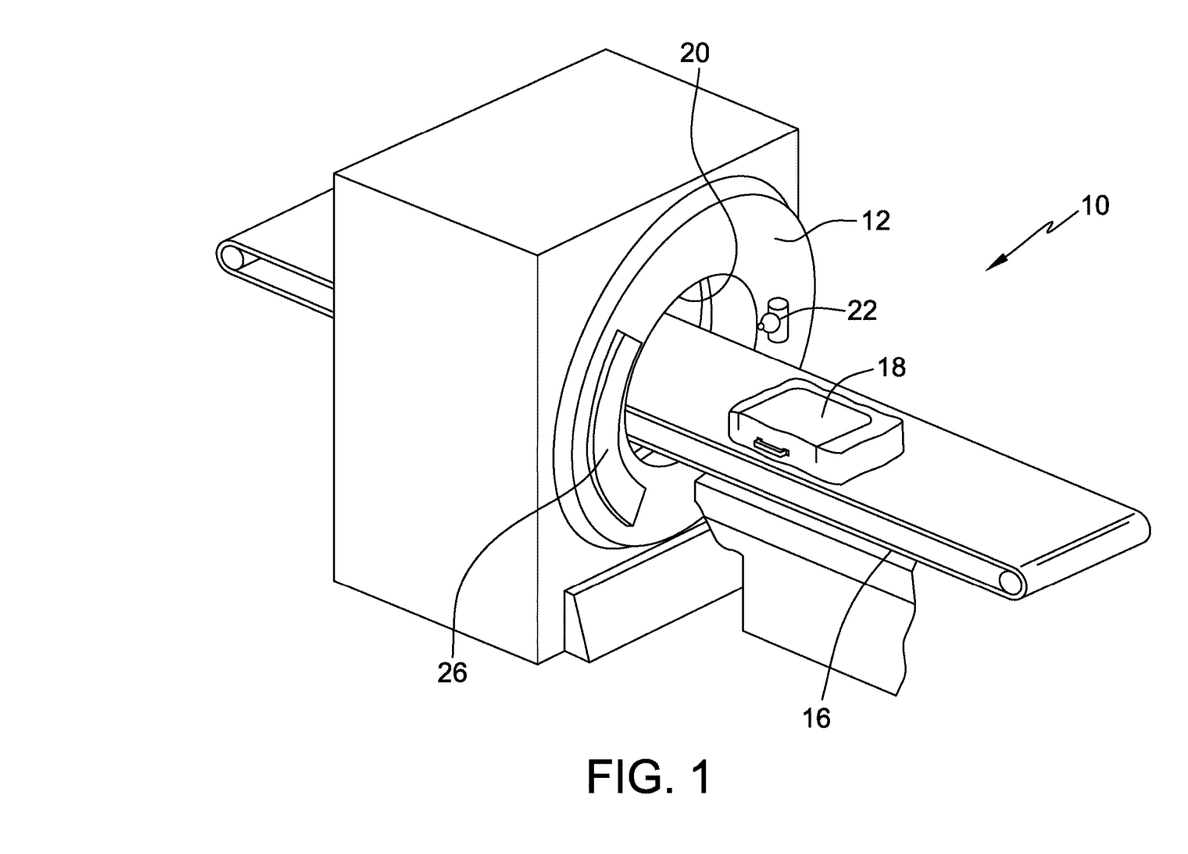
FIG. 1 is a perspective view of an exemplary CT imaging system.

Referring now to FIG. 1, a computed tomography (CT) imaging system 10 is shown. CT imaging system 10 is shown having a gantry 12, which is representative of a CT scanner, a control system 14, and a motorized conveyor belt 16 for positioning an object 18, such as a piece of luggage, in a gantry opening 20 defined through gantry 12. Gantry 12 includes an x-ray source 22 that projects a fan beam of x-rays 24 toward a detector array 26 on the opposite side of gantry 12. Detector array 26 is formed by detector elements 28, which are radiation detectors that each produce a signal having a magnitude that represents and is dependent on the intensity of the attenuated x-ray beam after it has passed through object 18 being imaged.

Figure 2A:
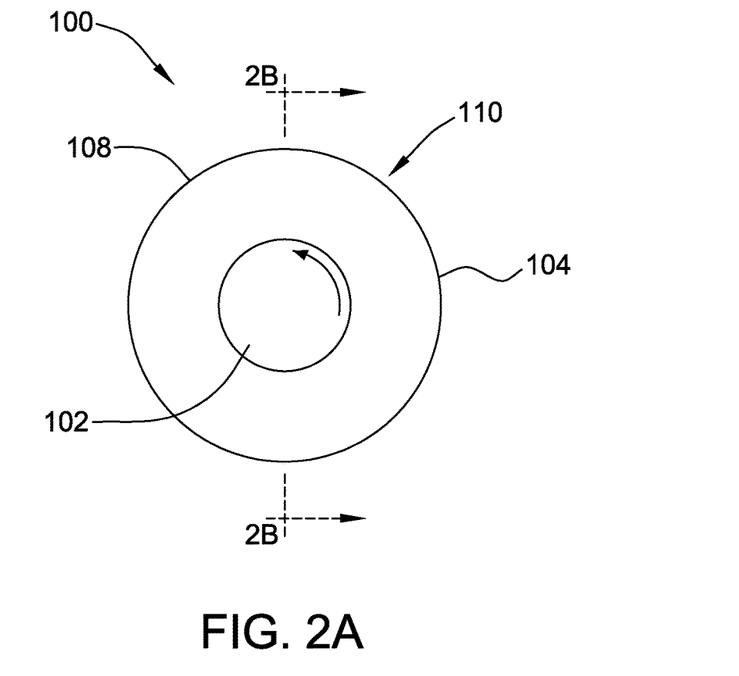
FIGS. 2A and 2B are schematic views of one example embodiment of small-diameter capsule slips rings (CSR) for use in a gantry system of the CT imaging system shown in FIG. 1.
Figure 2B:
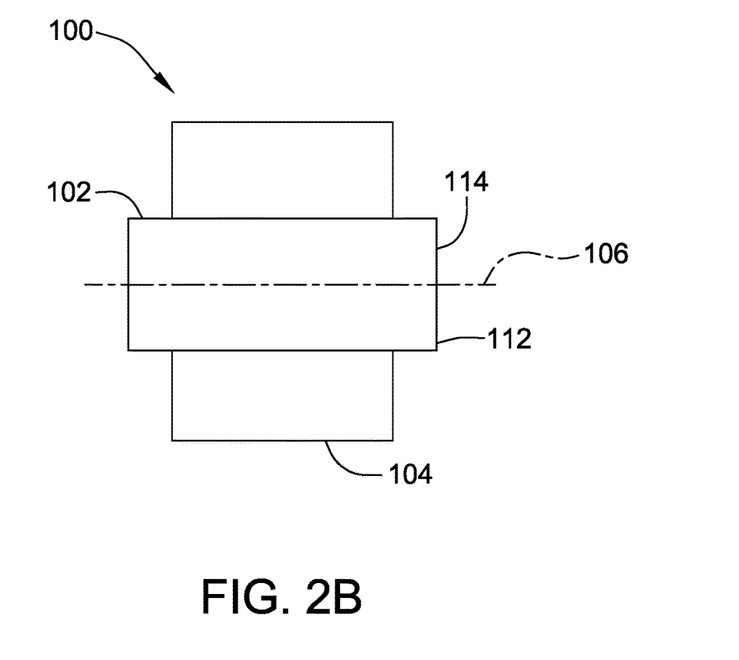

FIGS. 2A and 2B are schematic views of one example embodiment of small-diameter capsule slips rings (CSR) 100. FIG. 2B is a schematic cross-sectional view taken along line 2B-2B. Each CSR 100 includes a rotor 102 and a stator 104. Rotor 102 rotates about an axis of rotation 106 at an angular velocity of $\omega_{CSR}$. Although in the illustrated embodiment, stator 104 circumscribes rotor 102, it should be understood that there are numerous other relative orientations of rotor 102 and stator 104 that may be implemented. In the example embodiment, stator 104 is coaxial with rotor 102. In the illustrated embodiment, a stationary electrical connection 108 is defined on at least a portion of an exterior surface 110 of stator 104. In addition, a rotating electrical connection 112 is defined on at least a portion of an exterior surface 114 of rotor 102. The illustrated CSR 100 implements an electrical rotary joint, at its operating angular velocity $\omega_{CSR}$, for electrical communication thereacross.

Figure 3:
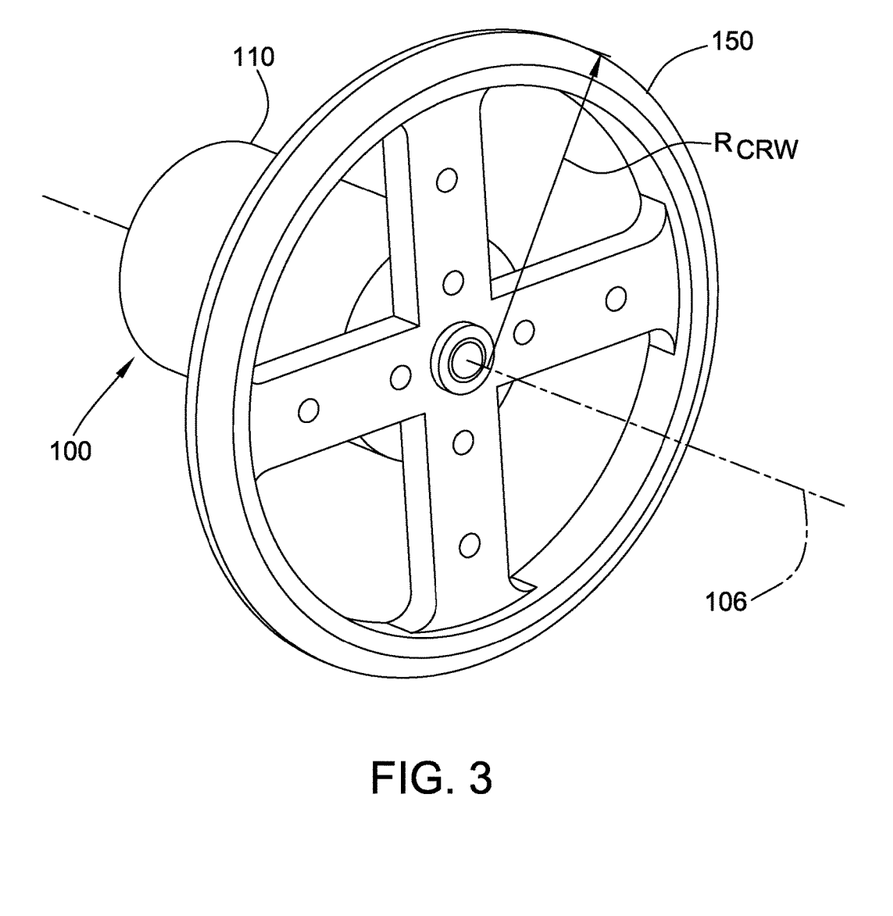
FIG. 3 is a perspective view of the example CSR shown in FIGS. 2A and 2B with a contact roller wheel (CRW) coupled thereto.

FIG. 3 is a perspective view of the example capsule slip ring (CSR) 100 with a contact roller wheel (CRW) 150 coupled thereto. In the illustrated embodiment, CRW 150 is rigidly connected to and coaxial with CSR 100. More specifically, CRW 150 is rigidly connected to CSR rotor 102 (shown in FIGS. 2A and 2B) such that CRW 150 rotates with rotor 102. CRW 150 may be connected to CSR 100 using any suitable method, such as adhesives and/or fasteners. CRW 150 is fabricated from an electrically conductive material, such as copper, brass, any other metal or conductive alloy, and/or other suitably conductive materials. In the illustrated embodiment, CRW 150 is electrically connected to rotating electrical connection 112 (shown in FIG. 2B) of CSR 100, such that any electrical potential of CSR 100 (e.g., an electrical potential initiated at stationary electrical connection 108, shown in FIG. 2A) is conveyed to CRW 150. CRW 150, as illustrated, has an outer radius $R_{CRW}$ and rotates about axis of rotation 106 (shown in FIGS. 2A and 2B) at an angular velocity of $\omega_{CRW}$. It should be understood that, because CRW 150 is coaxial with and rigidly attached to CSR 100, $\omega_{CRW}$ is equal to $\omega_{CSR}$. Although CRW 150 is depicted as a "wheel," it should be understood that any other generally annular, disc-like, or cylindrical conductive member may be connected to CSR 100 and function as described with respect to CRW 150.

Figure 4:
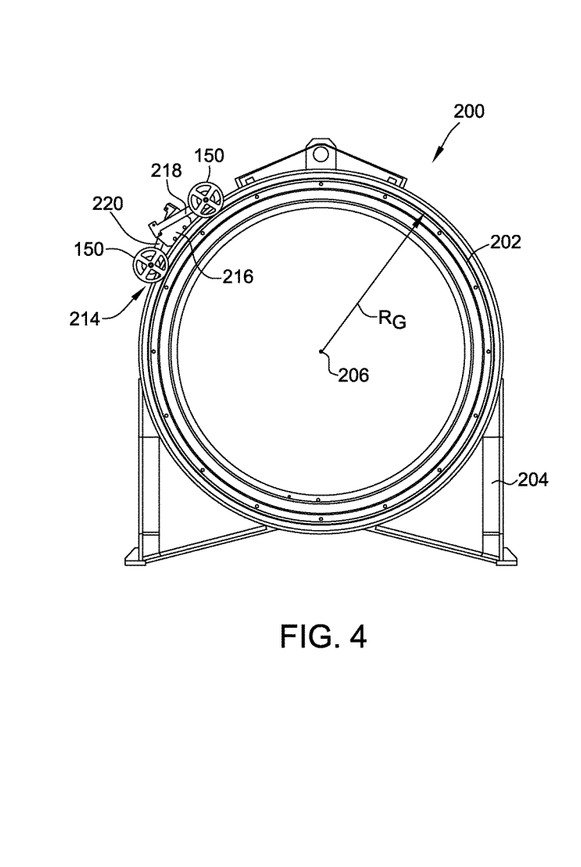
FIG. 4 is a front view of a first example embodiment of a gantry system.
Figure 5:
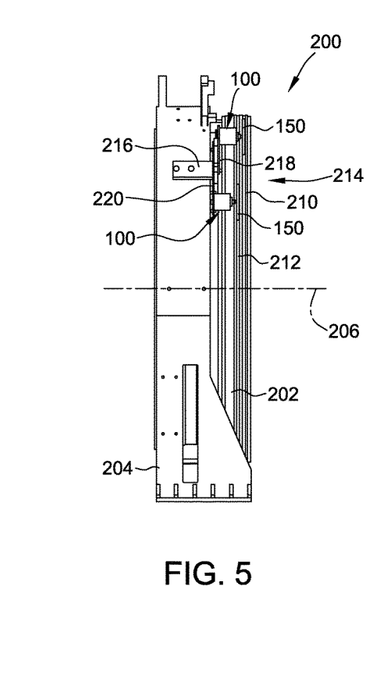
FIG. 5 is a side view of the gantry system shown in FIG. 4.
Figure 6:
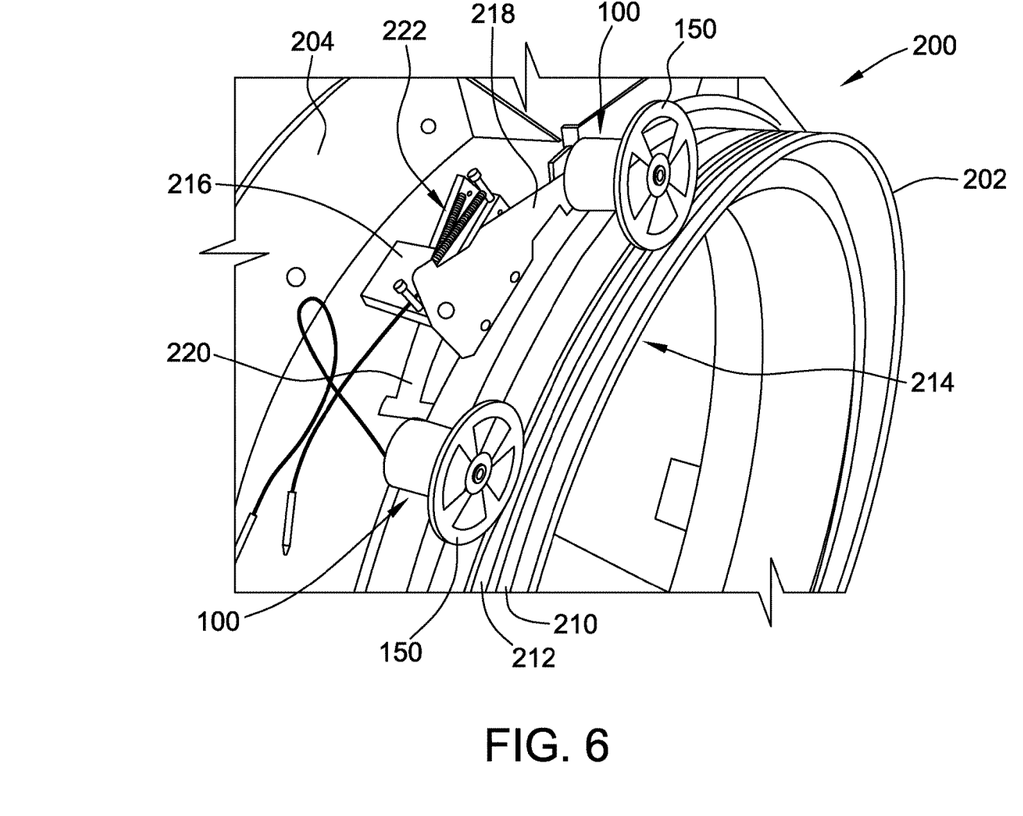
FIG. 6 is an enlarged perspective view of the gantry system shown in FIGS. 4 and 5.

FIGS. 4-6 illustrate a first example embodiment of a gantry system 200. More particularly, FIG. 4 is a front view of gantry system 200, FIG. 5 is a side view of gantry system 200, and FIG. 6 is an enlarged perspective view of gantry system 200. Gantry system 200 includes a large-diameter gantry 202 that is rotatable with respect to a frame 204 about an axis of rotation 206. Accordingly, in the illustrated embodiment, gantry 202 defines a system rotor of gantry system 200, and frame 204 defines a system stator of gantry system 200. Gantry 202 has an outer radius $R_G$ and is configured to rotate about axis of rotation 206 with an angular velocity of $\omega_G$. In the illustrated embodiment, two contact channels 210, 212 are disposed circumferentially about gantry 202. Each contact channel 210, 212 is fabricated from an electrically conductive material (e.g., copper, brass, any other metal or conductive alloy, and/or any other conductive material). In some embodiments, contact channels 210, 212 may be fabricated using a lathe. In other embodiments, contact channels 210, 212 may be fabricated by deposition of the conductive material onto an insulating substrate in which contact channel 210, 212 is machined. Each contact channel 210, 212 forms a conductive path that follows a trajectory of roughly constant radius (to within manufacturing tolerances) from axis of rotation 206. In the illustrated embodiment, that trajectory is roughly gantry radius $R_G$. It should be understood that although two contact channels 210, 212 are illustrated, in various other embodiments of gantry system 200, one contact channel or a plurality of contacts channels may be provided.

Gantry system 200, as illustrated, further includes two capsule slips rings (CSRs) 100 (shown in FIGS. 2A and 2B) having contact roller wheels (CRWs) 150 (shown in FIG. 3) coupled thereto. Each CRW 150 is placed in mechanical and electrical contact with one of contact channels 210, 212. Accordingly, the conductive CRW 150 and respective conductive contact channel 210, 212 are held at the same electrical potential. CSRs 100 are coupled to frame 204, in the example embodiment, via a bracket 216. Bracket 216 includes two lever arms 218, 220 to couple bracket 216 to each respective CSR 100. In the example embodiment, lever arms 218, 220 bias CSRs 100 and attached CRWs 150 against contact channels 210, 212 with a biasing mechanism, such as a pre-loading spring 222 (shown in FIG. 6). CRWs 150 are therefore maintained in robust electrical contact with contact channels 210, 212, which reduces or eliminates the effects of any imperfections in the geometry of gantry 202 and/or contact channels 210 and/or 212, imperfections in the finish and geometry of CRWs 150, and/or small foreign objects or debris such as metal shavings between CRWs 150 and contact channel 210 and/or 212. It should be understood that alternative connection components to bracket 216 and/or alternative biasing mechanisms to spring 222 may be employed without departing from the scope of the disclosure. Moreover, it should be understood that gantry system 200 may include a housing (not shown) configured to surround gantry 202 and frame 204, thereby protecting the above-described components from accidental exterior contact (which may disrupt the connection between CRWs 150 and contact channels 210, 212).

In terms of electrical function, each contact channel 210, 212 is similar to an electrical channel, and thus two individual contact channels 210 and 212 form one circuit across a rotary joint 214 formed by contact channels 210 and 212, CRWs 150, and CSRs 100. The circuit across rotary joint 214 may transfer electrical power or data thereacross. Any number of contact channels 210, 212 may be disposed about gantry 202 to form as many circuits as desired. In one embodiment, additional contact channels may be spaced apart in a direction parallel to axis of rotation 206 to increase the number of circuits thereon.

With respect to gantry system 200, CSR rotor 102 (shown in FIGS. 2A and 2B) spins at a different rate (angular velocity $\omega_{CSR}$) than the system rotor, gantry 202, which spins at angular velocity $\omega_G$. The relationship between these angular velocities is similar to that of a gearing system. Specifically, for the illustrated embodiment, if CRW 150 has radius $R_{CRW}$ and contact channels 210, 212 have radius $R_{CC}$ (which is substantially equal to gantry radius $R_G$, in the illustrated embodiment), and gantry 202 has an angular velocity of $\omega_G$, then the angular velocity of CRW 150, $\omega_{CRW}$, is $$\omega_{CRW} = \frac{R_{CC}}{R_{CRW}} \omega_G$$

Because $R_{CC} \gg R_{CRW}$, in the example embodiment, and due to the gearing effect of CRW 150 and gantry 202, CSR 100 must be capable of spinning at much higher angular velocity than gantry 202. However, many CSRs 100 are rated to a much higher angular velocity than, for example, a large thru-bore slip ring, such that electrical transfer across rotary joint 214 (e.g., of power or data) is facilitated.

Although one CSR 100/CRW 150 assembly per contact channel is shown in the illustrated embodiment of FIGS. 4-6, it should be understood that a plurality of such assemblies may be included in gantry system 200 and be in contact with contact channels 210, 212. In particular, a plurality of such assemblies may be arranged circumferentially about gantry 202. This may provide redundancy of electrical contact in the case that one of the CSR 100/CRW 150 assemblies fail, or is knocked free from contact (despite pre-loading using biasing mechanism 222) with contact channels 210, 212, for example, by a large foreign object.

Although the illustrated embodiment of FIGS. 4-6 depicts contact channels 210, 212 as constituents of gantry 202 (the system rotor of gantry system 200), in alternative embodiments, contact channels may be constituents of the system stator of gantry system 200, as described further herein. However, whether the contact channels are part of the system rotor or system stator, CSR 100 is mounted to the other of the system rotor and system stator, or the "opposite" side of the rotary joint (e.g., rotary joint 214).

Figure 7:
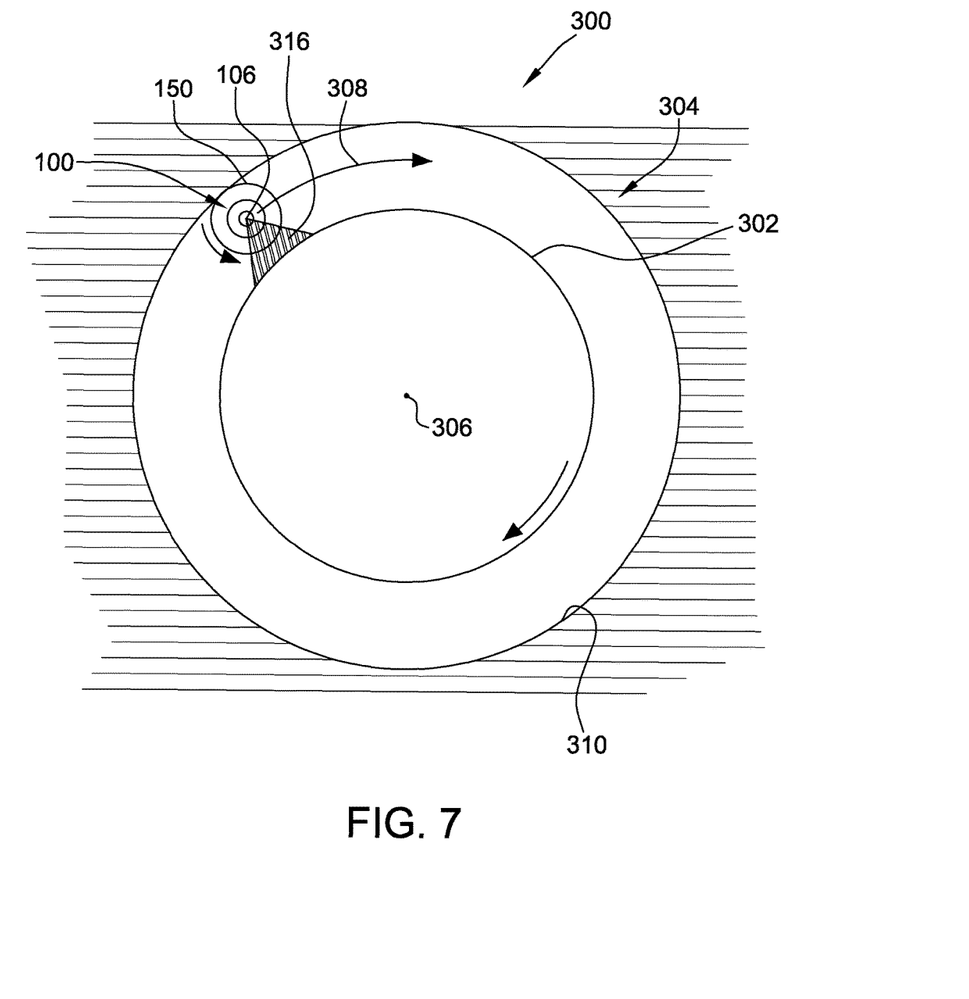
FIG. 7 is a schematic diagram of a second example embodiment of a gantry system.

FIG. 7 illustrates a second example embodiment of a gantry system 300. In particular, in the illustrated embodiment, at least one contact channel is disposed circumferentially about a system stator of gantry system 300 (as opposed to being disposed circumferentially about a system rotor, as illustrated with respect to gantry system 200, shown in FIGS. 4-6).

Specifically, gantry system 300 includes a gantry 302 (defining the system rotor of gantry system 300) and a frame 304 or other stationary component (defining the system stator of gantry system 300). Gantry 302 rotates about an axis of rotation 306. One capsule slip ring (CSR) 100/ contact roller wheel (CRW) 150 assembly is coupled to gantry 302 via a bracket 316. It should be understood that FIG. 7 is a simplified diagram and many elements of gantry system 300, such as bracket 316, may be implemented in a similar manner to corresponding elements of gantry system 200, such as bracket 216 (shown in FIGS. 4-6). CRW 150 is biased into mechanical and electrical contact with a contact channel 310 disposed about system stator 304. CSR 100 and CRW 150 rotate about axis of rotation 106. Moreover, the CSR 100/CRW 150 assembly rotates about a system axis of rotation 306, such that CSR axis of rotation 106 follows an orbit 308. Accordingly, in the illustrated embodiment, contact channel 310 is stationary with respect to system axis of rotation 306, and CRW 150 rotates and orbits along orbit 308 in contact with contact channel 310.

Figure 8:
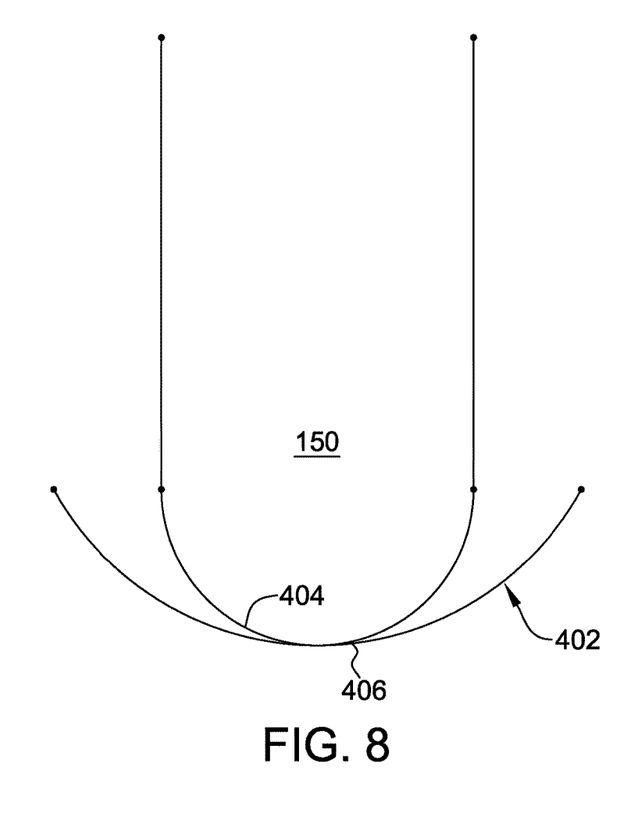
FIG. 8 is a schematic diagram of a first example mechanical connection between a CRW as shown in FIG. 3 and a contact channel of a gantry system.

FIG. 8 depicts a diagram of a first example mechanical connection between a contact roller wheel (CRW) 150 (shown in FIG. 3) and a contact channel 402 of a gantry system (e.g., contact channel 210 and/or 212 in gantry system 200, shown in FIGS. 4-6, and/or contact channel 310 in gantry system 300, shown in FIG. 7). As illustrated, CRW 150 has a convex profile 404, and contact channel 402 has a concave profile 406. Such complementary profiles 404, 406 promote mechanical contact between CRW 150 and contact channel 402 even in the case of small imperfections in either profile 404, 406 and/or slight jarring of either CRW 150 and/or contact channel 402.

Figure 9:
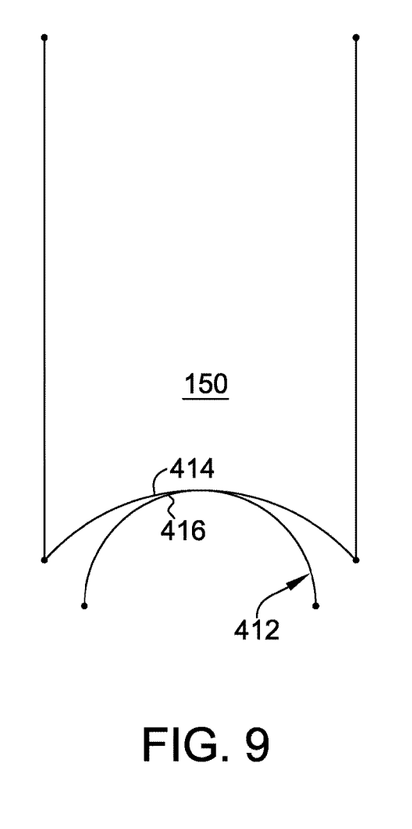
FIG. 9 is a schematic diagram of a second example mechanical connection between a CRW as shown in FIG. 3 and a contact channel of a gantry system.

FIG. 9 depicts a diagram of a second example mechanical connection between a contact roller wheel (CRW) 150 (shown in FIG. 3) and a contact channel 412 of a gantry system (e.g., contact channel 210 and/or 212 in gantry system 200, shown in FIGS. 4-6, and/or contact channel 310 in gantry system 300, shown in FIG. 7). As illustrated, CRW 150 has a concave profile 414, and contact channel 412 has a convex profile 416. Such complementary profiles 414, 416 promote mechanical contact between CRW 150 and contact channel 412 even in the case of small imperfections in either profile 414, 416 and/or slight jarring of either CRW 150 and/or contact channel 412. It should be understood that although two example profiles of CRW 150 and contact channels 402, 412 have been provided, any number of profiles may be employed in a gantry system, as long as the profiles are suitable to facilitate mechanical (and, thereby, electrical) connection between CRW 150 and the respective contact channel.

Exemplary embodiments of methods and systems are described above in detail. The methods and systems are not limited to the specific embodiments described herein, but rather, components of systems and/or steps of the methods may be used independently and separately from other components and/or steps described herein. Accordingly, the exemplary embodiment can be implemented and used in connection with many other applications not specifically described herein. For example, the above-described capsule slip ring (CSR) rotary joint may be implemented in any suitable rotatable-to-stationary system, including those with large thru-bore system rotors.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A gantry system comprising:
   a gantry that rotates about a system axis of rotation;
   a frame that is stationary with respect to the gantry;
   a first conductive contact channel and a second conductive contact channel disposed on one of the gantry and the frame; and
   a first capsule slip ring (CSR) and a second CSR coupled to the other of the gantry and the frame, the first CSR having a first contact roller wheel (CRW) coupled thereto, and the second CSR having a second CRW coupled thereto, the first CRW in mechanical contact with the first conductive contact channel and the second CRW in mechanical contact with the second conductive contact channel such that the first CSR and the second CSR form an electrical rotary joint between the gantry and the frame.

2. The gantry system of claim 1, wherein the first conductive contact channel and the second conductive channel are disposed on the gantry, and wherein the first CSR and the second CSR are coupled to the frame.

3. The gantry system of claim 1, wherein the first CSR is coupled to the frame via a bracket that biases the first CRW against the first conductive contact channel.

4. The gantry system of claim 1, wherein the first conductive contact channel and the second conductive contact channel are disposed on the frame, and wherein the first CSR and the second CSR are coupled to the gantry.

5. The gantry system of claim 1, wherein the gantry has a first diameter, and wherein the first CSR and the second CSR respectively have a second and third diameter each smaller than the first diameter.

6. The gantry system of claim 1, wherein the electrical rotary joint is configured to transfer at least one of data and power between the gantry and the frame.

7. The gantry system of claim 3, wherein the second CSR is coupled to the frame via the bracket that biases the second CRW against the second conductive contact channel.

* * * * *